(12) United States Patent
Neumann

(10) Patent No.: US 12,073,942 B2
(45) Date of Patent: Aug. 27, 2024

(54) METHODS AND SYSTEMS FOR DYNAMIC CONSTITUTIONAL GUIDANCE USING ARTIFICIAL INTELLIGENCE

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 1155 days.

(21) Appl. No.: 16/863,036

(22) Filed: Apr. 30, 2020

(65) Prior Publication Data
US 2021/0343407 A1    Nov. 4, 2021

(51) Int. Cl.
| | |
|---|---|
| *G16H 50/20* | (2018.01) |
| *G06F 18/214* | (2023.01) |
| *G06F 18/2413* | (2023.01) |
| *G06F 18/2415* | (2023.01) |
| *G06N 3/00* | (2023.01) |
| *G06N 3/02* | (2006.01) |

(Continued)

(52) U.S. Cl.
CPC ........ *G16H 50/20* (2018.01); *G06F 18/2155* (2023.01); *G06F 18/24147* (2023.01); *G06F 18/24155* (2023.01); *G06N 3/00* (2013.01); *G06N 3/02* (2013.01); *G06N 20/00* (2019.01); *G06V 10/762* (2022.01); *G06V 10/7753* (2022.01); *G16H 50/30* (2018.01); *G05B 2219/21002* (2013.01)

(58) Field of Classification Search
CPC .... G16H 50/20; G16H 50/30; G06F 18/2155; G06F 18/24147; G06F 18/24155; G06N 20/00; G06N 3/00; G06N 3/02; G06V 10/762; G06V 10/764; G06V 10/7753
See application file for complete search history.

(56) References Cited

U.S. PATENT DOCUMENTS

| | | |
|---|---|---|
| 7,624,028 B1 | 11/2009 | Brown |
| 8,417,537 B2 | 4/2013 | Apacible et al. |

(Continued)

OTHER PUBLICATIONS

Ravi et al., Deep Learning for Health Informatics, 21(1) IEEE J of Biomedical and Health Informatics 4-21 (Jan. 2017) (Year: 2017).*

(Continued)

*Primary Examiner* — Jordan L Jackson
(74) *Attorney, Agent, or Firm* — Caldwell Intellectual Property Law

(57) ABSTRACT

A system for dynamic conditional guidance using artificial intelligence. The system includes a computing device, designed and configured to c calculate a diagnostic output using a biological extraction related to a user, and a first machine-learning process, wherein the diagnostic output identifies a prognostic label and an ameliorative label; classify, using a physiological classifier and a first classification algorithm, the diagnostic output to a physiological state for the user; generate a vector output for the physiological state for the user, using a clustering algorithm; receive a user input generated in response to the diagnostic output; update the vector output using the user input; and identify a recommendation for the user, utilizing the updated vector output.

20 Claims, 7 Drawing Sheets

(51) Int. Cl.
    *G06N 20/00*         (2019.01)
    *G06V 10/762*      (2022.01)
    *G06V 10/774*      (2022.01)
    *G16H 50/30*       (2018.01)

(56) References Cited

U.S. PATENT DOCUMENTS

| | | |
|---|---|---|
| 8,620,591 B2 | 12/2013 | Wegerich |
| 10,599,984 B1 * | 3/2020 | Wubbels ................ G16H 30/40 |
| 2013/0054272 A1 | 2/2013 | Rangadass et al. |
| 2014/0188507 A1 | 7/2014 | Chen et al. |
| 2016/0350194 A1 | 12/2016 | Mohan et al. |
| 2017/0109806 A1 | 4/2017 | Adoni et al. |
| 2017/0357760 A1 * | 12/2017 | Han ....................... G06N 20/00 |
| 2018/0165418 A1 | 6/2018 | Swartz et al. |

OTHER PUBLICATIONS

Jan et al., Ensemble approach for developing a smart heart disease prediction system using classification algorithms, 9 Research Reports in Clinical Cardiology 33-45 (Year: 2018).*

* cited by examiner

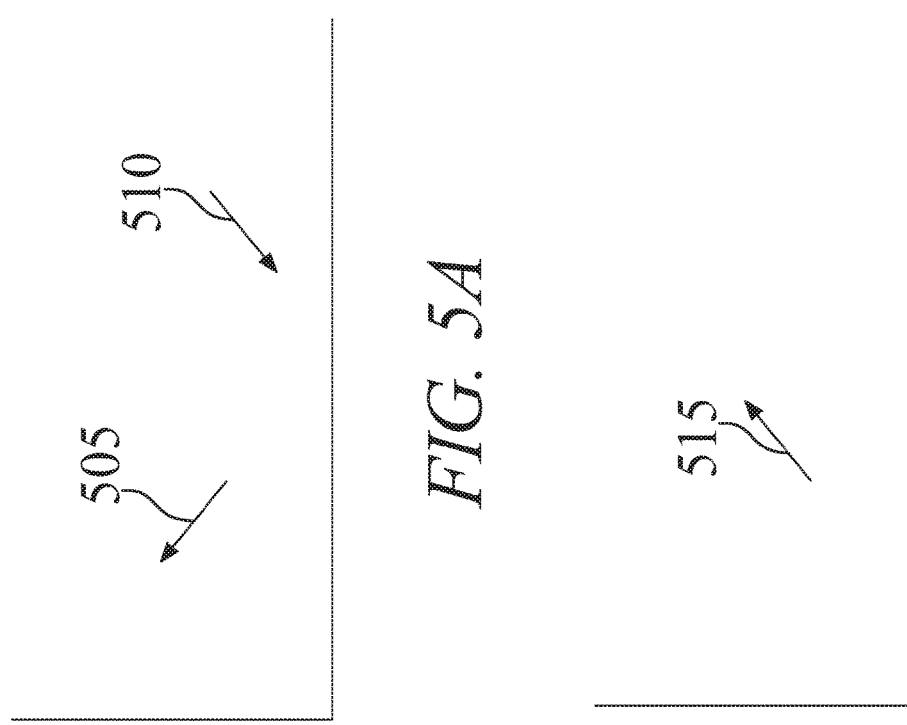

METHODS AND SYSTEMS FOR DYNAMIC CONSTITUTIONAL GUIDANCE USING ARTIFICIAL INTELLIGENCE

FIELD OF THE INVENTION

The present invention generally relates to the field of artificial intelligence. In particular, the present invention is directed to methods and systems for dynamic constitutional guidance using artificial intelligence.

BACKGROUND

Accurate assessments and recommendations for a physiological state of a user can be challenging. Recommendations that are not personalized can sometimes do more harm than good. Identifying recommendations that are individualized and aimed at optimizing one's physiological state remains to be seen.

SUMMARY OF THE DISCLOSURE

In an aspect, a system for dynamic conditional guidance using artificial intelligence, the system comprising a computing device, the computing device designed and configured to calculate a diagnostic output using a biological extraction related to a user, and a first machine-learning process, wherein the diagnostic output identifies a prognostic label and an ameliorative label; classify, using a physiological classifier and a first classification algorithm, the diagnostic output to a physiological state for the user; generate a vector output for the physiological state for the user, using a clustering algorithm; receive a user input generated in response to the diagnostic output; update the vector output using the user input; and identify a recommendation for the user, utilizing the updated vector output.

In an aspect, a method of dynamic conditional guidance using artificial intelligence, the method comprising: calculating by a computing device, a diagnostic output using a biological extraction related to a user, and a first machine-learning process, wherein the diagnostic output identifies a prognostic label and an ameliorative label; classifying by the computing device, using a physiological classifier and a first classification algorithm, the diagnostic output to a physiological state for the user; generating by the computing device, a vector output for the physiological state for the user, using a clustering algorithm; receiving by the computing device, a user input generated in response to the diagnostic output; updating by the computing device, the vector output using the user input; and identifying by the computing device, a recommendation for the user, utilizing the updated vector output.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 5A-B are diagrammatic representations of vector outputs;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for dynamic conditional guidance using artificial intelligence. In an embodiment, a biological extraction is utilized to generate a diagnostic output. A physiological classifier utilizes the diagnostic output and a first classification algorithm to output a physiological state. A vector is generated in n-dimensional space using a clustering algorithm to identify recommendations for a user, based on user inputs.

Figure 1:
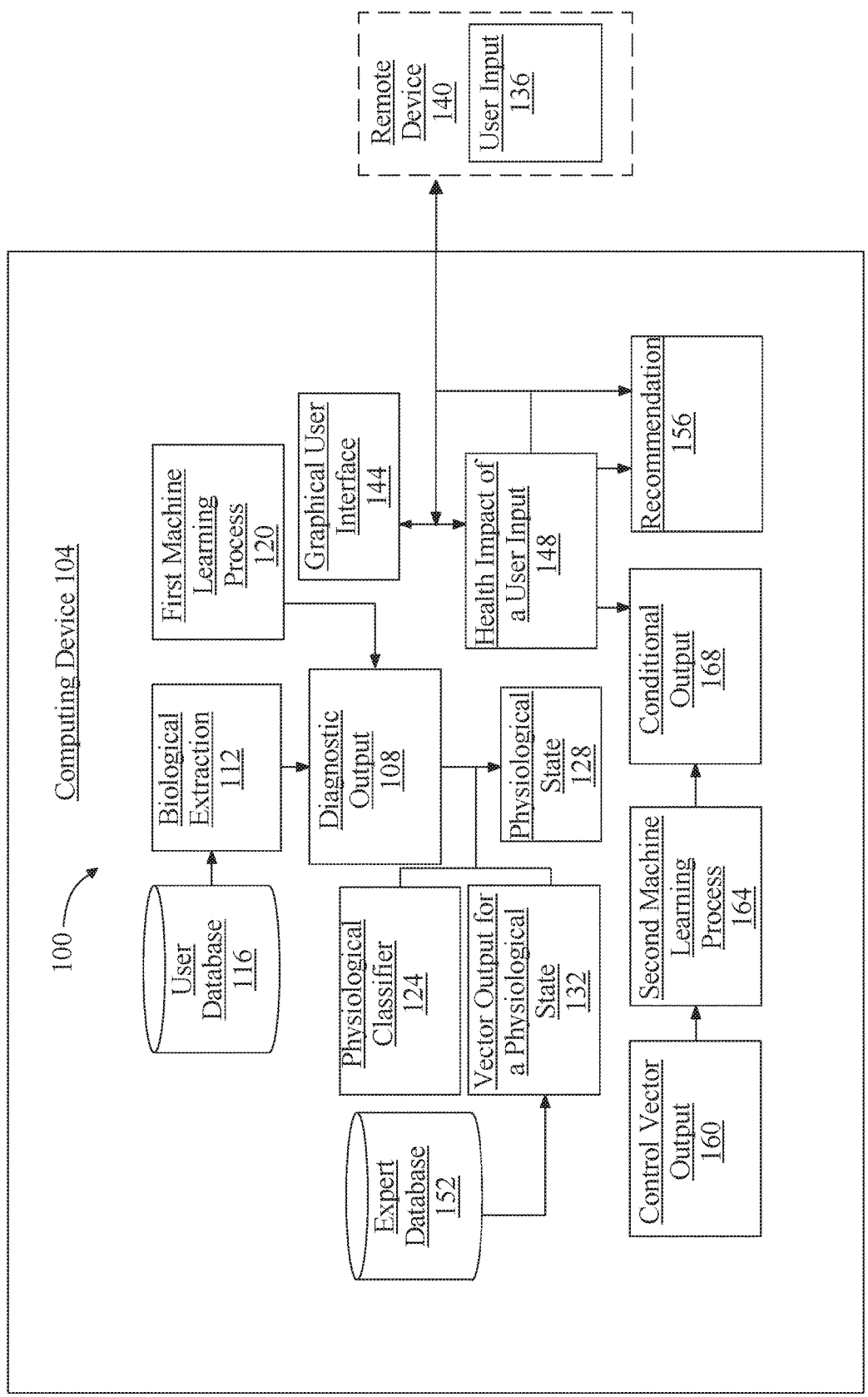
FIG. 1 is a block diagram illustrating an exemplary embodiment of a system for dynamic conditional guidance using artificial intelligence.

Referring now to FIG. 1, an exemplary embodiment of a system 100 for dynamic constitutional guidance using artificial intelligence is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to calculate a diagnostic output 108. A "diagnostic output," as used in this disclosure, is data containing a prognostic label and an ameliorative label. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or heathy aging. At least a prognostic label may be associated with a physical and/or somatic condition, a mental condition such as a mental illness, neurosis, or the like, or any other condition affecting human health that may be associated with one or more elements of physiological state data as described above in more detail. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, *Leishmania*, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. An ameliorative label may contain therapies, treatments, and/or lifestyle or dietary choices that may alleviate conditions associated with prognostic labels. An ameliorative label may contain therapies, treatments, and/or lifestyle or dietary choices that may alleviate conditions associated with prognostic labels. Computing device 104 generates a diagnostic output 108 by identifying, a current condition of the user utilizing a first training set, said first training set including a plurality of data entries, each first data entry of the plurality of data entries including an element of physiological state data and a correlated first prognostic label. Computing device 104 identifies, an ameliorative output related to the current condition of the user as a function of the identified current condition of the user and a second training set, said second training set including a plurality of second data entries, each second data entry including a second prognostic label and a correlated ameliorative label. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

With continued reference to FIG. 1, computing device 104 calculates a diagnostic output 108 using a biological extraction related to a user. A "biological extraction," as used in this disclosure, is an element of data including at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices 104; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure. As a non-limiting example, biological extraction 112 may include a psychological profile; the psychological profile may be obtained utilizing a questionnaire performed by the user.

Still referring to FIG. 1, physiological state data may include genomic data, including deoxyribonucleic acid (DNA) samples and/or sequences, such as without limitation DNA sequences or other genetic sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface 144 object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *Cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter* smithies' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, *Bacteroides vulgates', Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen-based breath tests, fructose-based breath tests, *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vasodilation and vasoconstriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100. User data may include a profile, such as a psychological profile, generated using previous item selections by the user; profile may include, without limitation, a set of actions and/or navigational actions performed as described in further detail below, which may be combined with biological extraction 112 data and/or other user data for processes such as classification to user sets as described in further detail below.

Still referring to FIG. 1, retrieval of biological extraction 112 may include, without limitation, reception of biological extraction 112 from another computing device 104 such as a device operated by a medical and/or diagnostic professional and/or entity, a user client device, and/or any device suitable for use as a third-party device as described in further detail below. Biological extraction 112 may be received via a questionnaire posted and/or displayed on a third-party device as described below, inputs to which may be processed as described in further detail below. Alternatively or additionally, biological extraction 112 may be stored in and/or retrieved from a user database 116. User database 116 may include any data structure for ordered storage and retrieval of data, which may be implemented as a hardware or software module. A user database 116 may be implemented, without limitation, as a relational database, a key-value retrieval datastore such as a NOSQL database, or any other format or structure for use as a datastore that a person skilled in the art would recognize as suitable upon review of the entirety of this disclosure. A user database 116 may include a plurality of data entries and/or records corresponding to user tests as described above. Data entries in a user database 116 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 116 may reflect categories, cohorts, and/or populations of data consistently with this disclosure. User database 116 may be located in memory of computing device 104 and/or on another device in and/or in communication with system 100.

With continued reference to FIG. 1, and as noted above, retrieval of biological extraction may be performed multiple sequential and/or concurrent times, and any process using biological extract as described below may be performed multiple sequential and/or concurrent times; likewise, biological extract may include multiple elements of physiological data, which may be used in combination for any determination and/or other processes as described below.

With continued reference to FIG. 1, computing device 104 is configured to calculate a diagnostic output 108 using a first machine-learning process 120. Still referring to FIG. 1, selection of at least a machine-learning process may include selection of a machine-learning model, a training data set to be used in a machine-learning algorithm and/or to produce a machine-learning model, and/or a machine-learning algorithm such as lazy-learning and/or model production, or the like. Computing device 104 may be designed and configured to create a machine-learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Continuing to refer to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include current membership of support networks and current group performance targets as inputs, and maximized member participation as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs. Supervised machine-learning processes may include classification algorithms as defined above.

Still referring to FIG. 1, machine learning processes may include unsupervised processes. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

With continued reference to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 1, at least a machine-learning process may include a lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, computing device 104 is configured to classify, using a physiological classifier 124 and a first classification algorithm, a diagnostic output 108 to a physiological state for a user. Computing device 104 generates a physiological classifier 124 using a classification algorithm, defined as a process whereby a computing device 104 derives, from training data, a model known as a "classifier" for sorting inputs into categories or bins of data. A "physiological classifier," as used in this disclosure, is a classifier that utilizes a diagnostic output 108 as an input, and outputs a physiological state. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate physiological classifier 124 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate physiological classifier 124 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may include generating a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify a diagnostic output 108 vector, to clusters representing physiological states.

With continued reference to FIG. 1, a "physiological state for a user," as used in this disclosure, is any characterization as to the overall current health of an individual. The overall health of an individual may include any indication as to the physical, mental, and/or social well-being of a user. The overall health of an individual may indicate any social determinants of health, such as the availability of resources to meet daily needs, exposure to crime, and violence, social support and social interactions, exposure to emerging technologies such as the Internet and cell phones, socioeconomic conditions, public safety, and/or transportation options. The overall health of an individual may indicate any health services, such as the availability of health services, cost of health services, and/or ability to obtain preventive services. The overall health of an individual may indicate any individual behaviors, such as the diet of an individual, the daily physical activity that a user obtains, the quantity of alcohol that a user consumes, and the like. The overall health of an individual may indicate any biological and/or genetic factors that affect a user such as the age of a user, the sex of a user, any inherited medical conditions such as sickle-cell anemia or cystic fibrosis, and the like. The overall health of an individual may include any risk factors, characteristic, condition, and/or behavior that increases the likelihood of an individual getting a disease or injury. For example, a behavioral risk factor such as smoking tobacco may indicate that a user is at risk for developing Type 2 Diabetes Mellitus. In yet another non-limiting example, a physiological risk factor such as having high blood pressure may indicate that a user is at risk for having a stroke or myocardial infarction. In yet another non-limiting example, an environmental risk factor such as a user who lives on a golf course and is exposed to chemicals such as glyphosate may be at greater risk of developing cancer such as non-Hodgkin lymphoma.

With continued reference to FIG. 1, computing device 104 is configured to generate a vector output for a physiological state 132 using a clustering algorithm. A "vector output for a physiological state," as used in this disclosure, is a data structure representing the physiological state. A vector output may include and/or be an "n" n-tuple of values, where n is at least two values. Each value of n-tuple of values may represent a measurement or other quantitative value associated with a given category of data, or attribute. A vector output may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance be advantageous where each vector represents a weighing of a characteristic vector output, and/or is to be compared to such a weighing of a characteristic vector output. A vector output may contain a label, identifying a physiological state associated with a particular vector output. For example, a first vector output intended for a physiological state of good health which may be reflected in a label identifying the first vector output as representing good health, while a second vector output intended for poor health may be reflected in a label identifying the second vector output as representing poor health. In an embodiment, a label may identify a particular about a physiological state of a user. For example, a label may identify a vector output as indicating a physiological state where the user is in good physical health but in poor mental health, as compared to a label that may identify a vector output as indicating a physiological state where the user is in fair physical health and poor social health.

A "clustering algorithm," as used in this disclosure, is a series of one or more calculations that groups a set of objects in such a way that objects in the same group or cluster are more similar to each other than to those in other groups or clusters. A clustering algorithm may include generating one or more clustering models. Clustering models may include for example, connectivity models such as hierarchical clustering. Clustering models may include for example, centroid models such as k-means algorithm. Clustering models may include for example, distribution models such as multivariate normal distributions using an expectation-maximization algorithm. Clustering models may include for example, density models such as density-based spatial clustering of applications with noise (DBSCAN) or ordering points to identify a clustering structure (OPTICS). Clustering models may include for example, subspace models such as bi-clustering. Clustering models may include for example, group models. Clustering models may include graph-based models such as highly connected subgraphs (HCS) clustering algorithm. Clustering models may include signed graph models. Clustering models may include neural models such as an unsupervised neural network With continued reference to FIG. 1, clustering algorithms and/or clustering models may be generated as hard and/or soft clusters. Clustering algorithms and/or clustering models may include hard clusters whereby each object belongs to a cluster or not. Clustering algorithms and/or clustering models may include soft clustering whereby each object may belong to each cluster to a certain degree. Clustering algorithms and/or clustering models may include strict partitioning clustering where each object belongs to exactly one cluster. Clustering algorithms and/or clustering models may include strict partitioning clustering with outliers where objects can also belong to no cluster and may be considered outliers. Clustering algorithms and/or clustering models may include overlapping clustering where objects may belong to more than one cluster. Clustering algorithms and/or clustering models may include hierarchical clustering where objects that belong to a child cluster may also belong to the parent cluster. Clustering algorithms and/or clustering models may include subspace clustering.

With continued reference to FIG. 1, computing device 104 calculates a plurality of vector outputs containing physiological states utilizing training data and a clustering algorithm. In an embodiment, a plurality of vector outputs may be generated based on the average physiological states identified in training data, and/or a statistical distribution of physiological state vector outputs, and/or a density of physiological state vector outputs. Computing device 104 converts a physiological state for the user to a vector output by transforming the physiological state for the user into n-dimensional space using an axis per category represented in n-tuple of values. This may include calculating an "n" n-tuple of values, for the physiological state for the user as described above in more detail. Computing device 104 calculates the distance in n-dimensional space between the plurality of vector outputs containing physiological states and the vector output containing the physiological state for the user. Computing device 104 may locate a condition vector output from the plurality of condition vector outputs closest to the vector output containing the physiological state for the user. Computing device 104 may select a condition vector output from the plurality of condition vector outputs that has the shortest distance and is located the closest to the vector output containing the physiological state for the user.

With continued reference to FIG. 1, computing device 104 may select a distance metric. In an embodiment, computing device 104 may utilize Euclidean distance which may measure distance by subtracting the distance between a user biological extraction profile 108 vector output and a condition vector output 128. In an embodiment, Euclidean distance may be calculated by a formula represented as: $E(x, y) = \sqrt{\sum_{i=0}(xi-yi)^2}$. In an embodiment, computing device 104 may utilize metric distance of cosine similarity which may calculate distance as the difference in direction between two vectors which may be represented as: similarity=cos 0=A× B÷∥A∥∥B∥. In an embodiment, distance may be measured utilizing one or more other measurements of distance, including for example Manhattan distance, Minkowski distance, Mahalanobis distance, and/or Jaccard distance.

With continued reference to FIG. 1, computing device 104 receives a user input 136 generated in response to a diagnostic output 108. A "user input," as used in this disclosure, is any response received from a user. A user input 136 may be received by computing device 104 from a remote device 140 operated by a user. A remote device 140 may include without limitation, a display in communication with computing device 104, where a display may include any display as described herein. Remote device 140 may include an additional computing device, such as a mobile device, laptop, desktop, computer and the like. Computing device 104 may receive a user input 136 entered on a graphical user interface 144 located on computing device 104. Graphical user interface 144 may include, without limitation, a form or other graphical element having display fields, where one or more elements of information may be displayed. Graphical user interface 144 may include sliders or other use inputs that may permit a user to select a particular entry. In an embodiment, a user may select one or more preferences the user has regarding support networks that may be of interest to the user. Graphical user interface 144 may include free form textual fields where a user can type in or enter one or more preferences that may be of pertinence or interest to the user.

With continued reference to FIG. 1, a user input 136 is generated in response to a diagnostic output 108. A user input 136 may identify any progress and/or lack of progress that a user has made in regard to an ameliorative label. For instance and without limitation, a diagnostic output 108 generated for a user by computing device 104 may contain an ameliorative label that suggests for a user to practice yoga five days per week. A user input 136 may be generated in response to the ameliorative label to identify how many times if any, a user practiced yoga, or how far a user came to implement a yoga practice. In yet another non-limiting example, a prognostic label may indicate that a user is likely to develop Type 2 Diabetes Mellites based on several risk factors that include being overweight, not being active, and smoking. In such an instance, a user may generate a user input 136 detailing how the user has taken steps to modify the user's risk factors, such as by staying active and starting to lose weight. In an embodiment, a user input may include a second biological extraction. A second biological extraction includes any biological extraction as described above in more detail.

With continued reference to FIG. 1, computing device 104 is configured to classify a user input 136 to determine the health impact of the user input 148, using a health classifier and a second classification algorithm. A "health classifier," as used in this disclosure, is any classifier that utilizes a user input as an input, and outputs a health impact of the user input. A second classification algorithm includes any classification algorithm suitable for use as first classification algorithm as described above in more detail. Computing device 104 classifies the user input 136 utilizing any of the classification algorithms as described above in more detail. A "health impact of a user input," as used in this disclosure, is any indication as to whether a user input 136 has a negative, positive, and/or neutral impact on the overall health and well-being of the user. For instance and without limitation, a user input 136 that details the user as still continuing to smoke would be classified as having a negative impact on the user's health. In yet another non-limiting example, a user input 136 that details the user as practicing a meditation sequence three nights each week would be classified as having a positive impact on the user's health. Computing device 104 classifies a user input 136 to determine the health impact of the user input 136 based on information that may be contained within expert database 152. Expert database 152 may be implemented as any data structure suitable for use as user database 116 as described above in more detail. Expert database 152 may contain entries describing health impacts of various user input 136 from experts in the field, as described below in more detail. Computing device 104 adjusts a vector output based on the health impact of the user input 136. Adjusting a vector output may include modifying and/or changing its location as represented in n-dimensional space. Adjusting a vector output may include changing the coordinates of a vector based on the impact of a user input 136.

With continued reference to FIG. 1, computing device 104 is configured to update a vector output using a user input 136. Updating a vector output may include changing the location of a vector output as represented in n-dimensional space, based on the health impact of a user input 148. In an embodiment, computing device 104 may convert the user input 136, and/or the health impact of the user input 136 into a vector represented in n-dimensional space. Computing device 104 may calculate the distance between the vector representing the user input 136 and/or the health impact of the user input 136 and the vector output for the physiological state for the user. Computing device 104 may adjust the coordinates of the vector output, using the calculated distance.

With continued reference to FIG. 1, computing device 104 is configured to identify a recommendation 156 for a user, utilizing an updated vector output. A "recommendation" as used in this disclosure, is any suggestion intended to improve the health of a user. A recommendation 156 may be generated based on information contained within a diagnostic output 108 and a user input 136. For instance and without limitation, a recommendation 156 may suggest that a user should go on a walk every night or that a user should aim to get at least thirty minutes of sunshine every day. A recommendation 156 may suggest that a user should get a minimum of seven hours of sleep each night. In an embodiment, a recommendation 156 may be represented as a vector, including any of the vectors as described herein. In an embodiment, a recommendation may be transmitted to remote device 140 operated by a user. In an embodiment, a recommendation may be transmitted to a third-party device operated by an informed advisor.

With continued reference to FIG. 1, computing device 104 is configured to identify a control vector output 160. A "control vector output," as used in this disclosure, is a vector representing the ideal health of a user. Computing device 104 evaluates the distance between an updated vector output and a control vector output 160. Evaluating the distance may include measuring the distance in n-dimensional space. Distance may be measured utilizing any of the distance measurements as described above in more detail. Computing device 104 locates a recommendation 156 to minimize the distance between an updated vector output and a control vector output 160. For instance and without limitation, computing device 104 may locate a recommendation 156 such as implementing a daily exercise program that will help minimize the distance between an updated vector output and a control vector output 160. In yet another non-limiting example, computing device 104 may locate a recommendation 156 such as taking a prescription medication that will help to minimize the distance between an updated vector output and a control vector output 160. Computing device 104 may transmit one or more recommendation 156 to remote device 140 operated by a user, utilizing any network methodology as described herein. Computing device 104 may display one or more recommendation 156 on a graphical user interface 144 located on computing device 104. Computing device 104 may locate one or more recommendation 156 as represented in n-dimensional space. For instance and without limitation, one or more recommendation 156 may be represented in n-dimensional space, and computing device 104 may locate one or more recommendation 156 situated between updated vector output and control vector output 160. Computing device 104 may measure the distance between the various recommendation 156 and select one or more recommendation 156 based on the distance of the recommendation 156 between updated vector output and/or control vector output 160. In an embodiment, computing device 104 may evaluate one or more identified recommendation 156 as compared to an ameliorative label for a user and/or a user input 136. For example, an ameliorative label may specify that a user was recommended to perform weight-bearing exercise two days each week. Computing device 104 may locate a recommendation 156 that suggests a user perform weight bearing exercise four days each week. Computing device 104 may evaluate a user input 136 which specifies that the user has been performing weight bearing exercise two days each week. In such an instance, computing device 104 may generate a recommendation 156 for the user to perform weight bearing exercise four days each week. In yet another non-limiting example, computing device 104 may locate a recommendation 156 located in n-dimensional space that contains a recommendation 156 for a user to quit smoking. Computing device 104 may evaluate an ameliorative label that suggests a user to quit smoking, and a user input 136 which details that the user was unable and is not ready to quit smoking. In such an instance, computing device 104 may disregard the recommendation 156 for the user to quit smoking since the user is unwilling and not ready to do so. Instead, computing device 104 may locate a second recommendation 156, such as a recommendation 156 for the user to get thirty minutes of exercise three days each week and suggest the second recommendation 156 to the user.

With continued reference to FIG. 1, computing device 104 is configured to calculate a conditional output 168 utilizing the distance measured between an updated vector output and a control vector output using a second machine-learning process 164. A second machine-learning process 164 includes any of the machine-learning processes as described above in more detail. A "conditional output," as used in this disclosure, is any indication as to the overall health and wellness of the user at that specific moment in time. A conditional output 168 may contain a numerical score, that may characterize the overall health of an individual. For example, a conditional output 168 may be ranked on a scale from 0 to 100, where a score of 0 may indicate that a user is in overall very poor health, while a score of 100 may indicate that a user is in excellent health. In an embodiment, computing device 104 may generate a numerical score and a corresponding description containing words, symbols, and/or graphics that may explain the numerical score in more detail. For instance and without limitation, a conditional output 168 that contains a numerical score of "52" may be accompanied by a textual explanation that details the user as being in fair health, with room for improvement. A conditional output may be dynamically evolving and change at specific moments in time when it is calculated. For instance and without limitation, a conditional output 168 may measure a score of 22 during an initial measurement, and the conditional output 168 may measure a score of 47 two months later after the user has made substantial lifestyle changes for example.

With continued reference to FIG. 1, computing device 104 is configured to convert a user input 136 to a user vector output. Converting a user input 136 may include transforming the user input 136 to be represented in n-dimensional space. This may be performed, utilizing any of the methodologies as described above in more detail. Computing device 104 calculates an ameliorative vector output for an ameliorative label. Calculating an ameliorative vector output includes transforming an ameliorative output to be represented in n-dimensional space. Computing device 104 analyzes the distance between a user vector output and an ameliorative vector output. Analyzing the distance may include measuring the distance between a user vector output and ameliorative vector output. Distance may be measured utilizing any of the distance measurements as described above in more detail. Computing device 104 generates a recommendation 156 for a user based on the measured distance between a user vector output and an ameliorative vector output. For instance and without limitation, a user vector output and an ameliorative vector output that has a large distance measurement between them, may be utilized to locate a recommendation 156 that will aid in minimizing the distance. For example, a user vector output that specifies the user has not started an exercise routine as recommended in an ameliorative output, may be utilized by computing device 104 to identify a recommendation 156 that suggests a user to engage in 30 minutes of walking each day, as a way to start to minimize the distance between a user vector output an ameliorative vector output.

Figure 2:
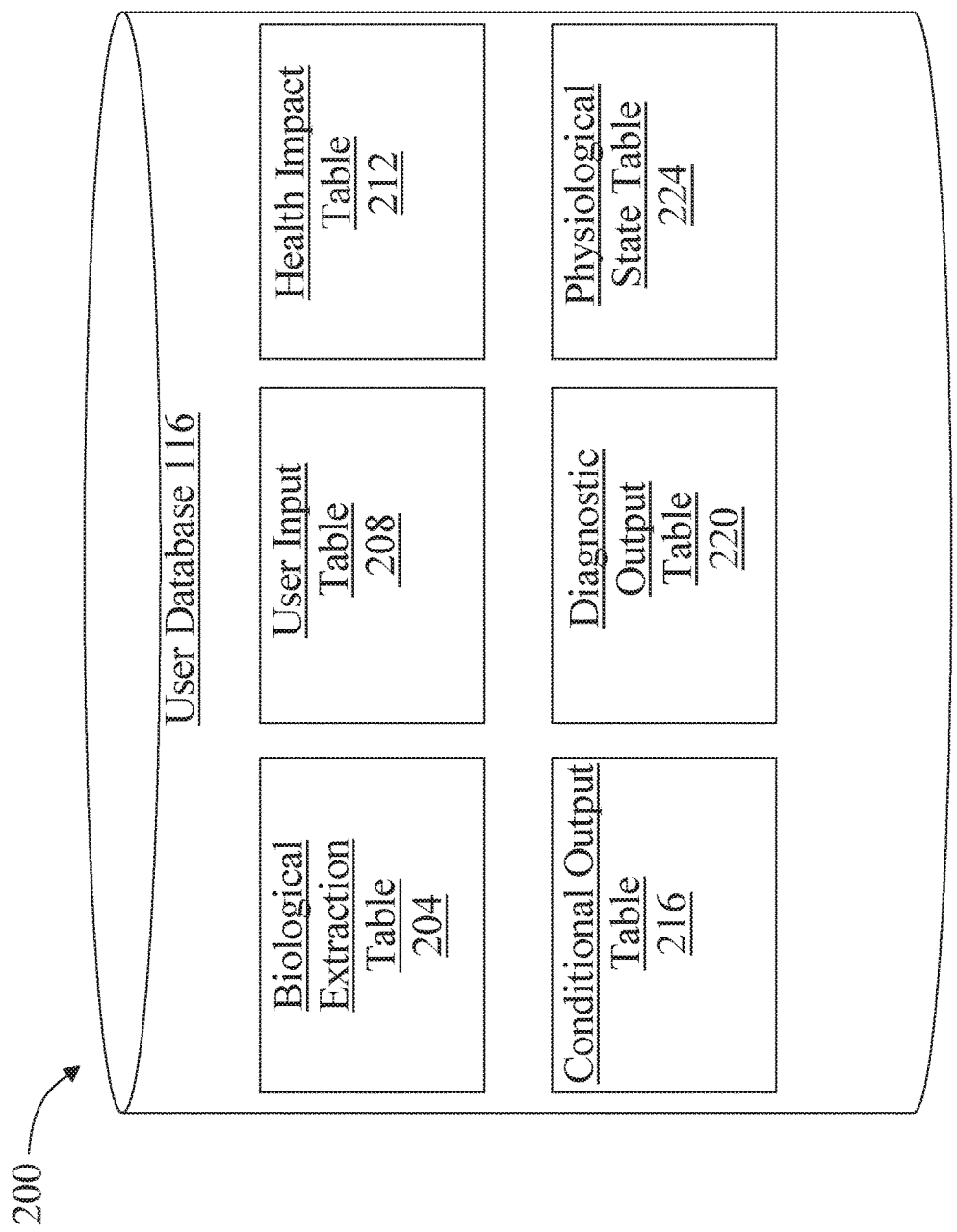
FIG. 2 is a block diagram illustrating an exemplary embodiment of a user database.

Referring now to FIG. 2, an exemplary embodiment 200 of user database 116 is illustrated. User database 116 may be implemented as any data structure as described above in more detail in reference to FIG. 1. One or more tables contained within user database 116 may include biological extraction table 204; biological extraction table 204 may include one or more biological extractions pertaining to a user. For instance and without limitation, biological extraction table 204 may include a blood sample analyzed for intracellular and extracellular nutrient levels. One or more tables contained within user database 116 may include user input table 208; user input table 208 may include one or more user input 136 generated by a user. For instance and without limitation, user input table 208 may include a self-report generated by the user detailing that the user practiced a yoga sequence three times during the previous week. One or more tables contained within user database 116 may include health impact table 212; health impact table 212 may include one or more health impacts of one or more user inputs. For instance and without limitation, health impact table 212 may contain an entry detailing that a user input 136 specifying that a user consumes eight servings of vegetables each day as having a positive health impact. One or more tables contained within user database 116 may include conditional output table 216; conditional output table 216 may include one or more conditional output 168 calculated for a user. For instance and without limitation, conditional output table 216 may contain an overall health score of the user as a 67, taken at a specific moment in time. One or more tables contained within user database 116 may include diagnostic output table 220; diagnostic output table 220 may include one or more diagnostic output 108 for a user. For instance and without limitation, diagnostic output table 220 may contain a diagnostic output 108 of leaky gut syndrome. One or more tables contained within user database 116 may include physiological state table 224; physiological state table 224 may contain one or more physiological states calculated for a user. For instance and without limitation, physiological state table 224 may contain an entry specifying that a user has been classified to a physiological state where the user is in overall excellent physical and mental health.

Figure 3:
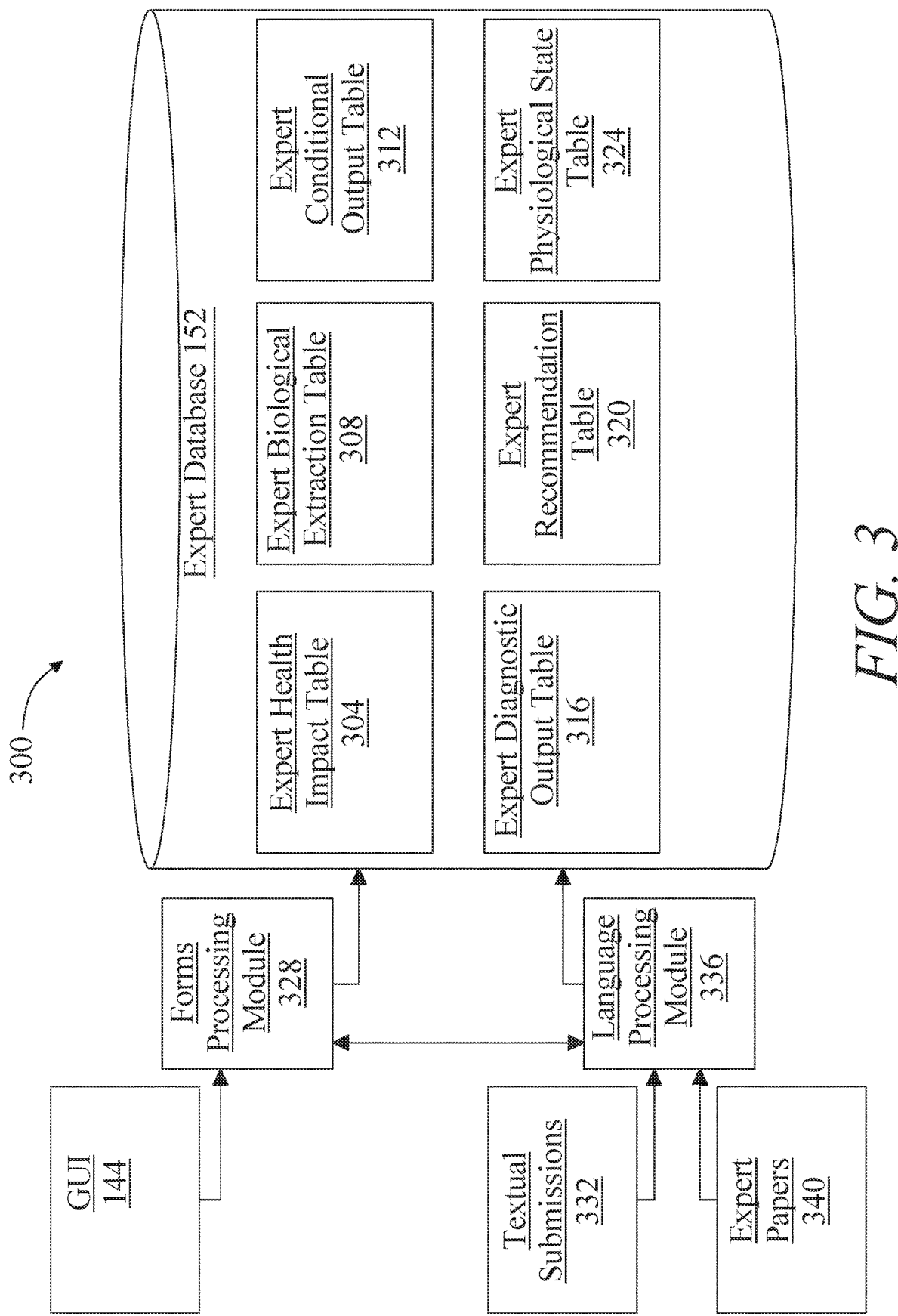
FIG. 3 is a block diagram illustrating an exemplary embodiment of an expert database.

Referring now to FIG. 3, an exemplary embodiment 300 of expert database 152 is illustrated. Expert database 152 may, as a non-limiting example, organize data stored in the expert database 152 according to one or more database tables. One or more database tables may be linked to one another by, for instance, common column values. For instance, a common column between two tables of expert database 152 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 3, one or more database tables in expert database 152 may include, as a non-limiting example, an expert health impact table 304; an expert health impact table 304 may include expert information relating to the health impact of user input 136. One or more database tables in expert database 152 may include, as a non-limiting example, an expert biological extraction table 308; expert biological extraction table 308 may include expert information relating to biological extractions 112. One or more database tables in expert database 152 may include, expert conditional output table 312; expert conditional output table 312 may include expert information relating to conditional output 168. One or more database tables in expert database 152 may include, expert diagnostic output table 316; expert diagnostic output table 316 may include expert information relating to diagnostic output 108. One or more database tables in expert database 152 may include, expert recommendation table 320; expert recommendation 156 table 320 may include expert information relating to recommendations 156. One or more database tables in expert database 152 may include expert physiological state table 324; expert physiological state table 324 may include expert information relating to physiological states.

In an embodiment, and still referring to FIG. 3, a forms processing module 328 may sort data entered in a submission via a graphical user interface 144 receiving expert submissions by, for instance, sorting data from entries in the graphical user interface 144 to related categories of data; for instance, data entered in an entry relating in the graphical user interface 144 to a biological extraction 112, which may be provided to expert biological extraction table 308, while data entered in an entry relating to member enhancement factors 168, which may be provided to expert member enhancement table 324. Where data is chosen by an expert from pre-selected entries such as drop-down lists, data may be stored directly; where data is entered in textual form, a language processing module may be used to map data to an appropriate existing label, for instance using a vector similarity test or other synonym-sensitive language processing test to map data to existing labels and/or categories. Similarly, data from an expert textual submission 332, such as accomplished by filling out a paper or PDF form and/or submitting narrative information, may likewise be processed using language processing module.

Still referring to FIG. 3, a language processing module 336 may include any hardware and/or software module. Language processing module 336 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 3 language processing module 336 may compare extracted words to categories of data to be analyzed; such data for comparison may be entered on computing device 104 as described above using expert data inputs or the like. In an embodiment, one or more categories may be enumerated, to find total count of mentions in such documents. Alternatively or additionally, language processing module 336 may operate to produce a language processing model. Language processing model may include a program automatically generated by at least a server and/or language processing module 336 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 3, language processing module 336 and/or computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 336 may combine two or more approaches. For instance, and without limitation, machine-learning program may use a combination of Naive-Bayes (NB), Stochastic Gradient Descent (SGD), and parameter grid-searching classification techniques; the result may include a classification algorithm 132 that returns ranked associations.

Continuing to refer to FIG. 3, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 3, language processing module 336 may use a corpus of documents to generate associations between language elements in a language processing module 336, and computing device 104 may then use such associations to analyze words extracted from one or more documents. Documents may be entered into computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, computing device 104 may automatically obtain the document using such an identifier, for instance by submitting a request to a database or compendium of documents such as JSTOR as provided by Ithaka Harbors, Inc. of New York.

With continued reference to FIG. 3, data may be extracted from expert papers 340, which may include without limitation publications in medical and/or scientific journals, by language processing module 336 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Figure 4:
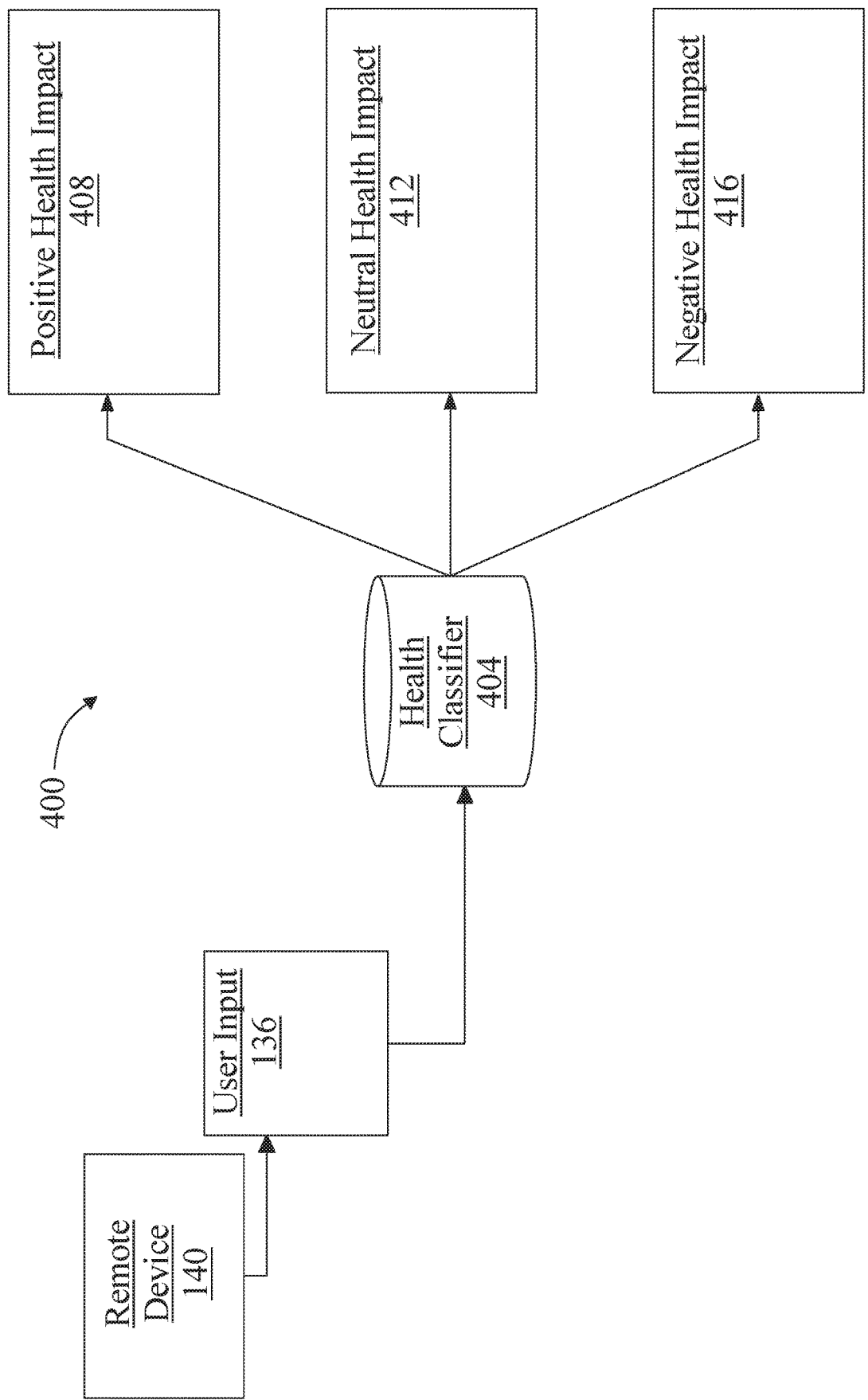
FIG. 4 is a diagrammatic representation of a health classifier.

Referring now to FIG. 4, an exemplary embodiment of health classifier is illustrated. In an embodiment, computing device 104 receives a user input 136 from a remote device 140, operated by the user. Computing device 104 receives the user input 136 utilizing any network methodology as described herein. Health classifier includes any of the health classifiers as described above in more detail in reference to FIG. 1. Health classifier 404 classifies a user input 136 to determine a health impact of the user input 136 using a second classification algorithm. A second classification algorithm includes any classification algorithm suitable for first classification algorithm as described above in more detail. For instance and without limitation, a second classification algorithm may include a naïve Bayes classifier, a fisher's linear discriminant classifier, a k-nearest neighbor, a random forest, a neural network, a decision tree, a logistic regression algorithm, a support vector machine algorithm, a stochastic gradient descent algorithm, a kernel approximation algorithm and the like. Health classifier 404 utilizes a classification algorithm to determine a health impact of the user input. A health impact, includes any of the health impacts as described above in more detail in reference to FIG. 1. In an embodiment, a health impact may include a positive health impact 404, such as when a user input 136 is associated with positive health changes. For example, a user input 136 that specifies that a user takes three weeks of vacation time each year may be classified as a positive health impact 408. In an embodiment, a health impact may include a neutral health impact 412, such as when a user input 136 is associated with neutral health changes. For example, a user input 136 that specifies that a user has not lost any weight and has not gained any weight may be classified as a neutral health impact 412. In an embodiment, a health impact may include a negative health impact 416, such as when a user input 136 is associated with negative health changes. For example, a user input 136 that specifies that a user continues to smoke two packs of cigarettes each day may be classified as a negative health impact. User input 136 may be classified to different categories of health impact based on one or more expert inputs contained within expert database 152.

Referring now to FIGS. 5A and 5B, an exemplary embodiment of vector outputs is illustrated. Referring to FIG. 5A, in an embodiment, one or more vector outputs, 505 may be represented in n-dimensional space. In an embodiment, vector output 505 may represent a vector output generated for the physiological state for the user utilizing a clustering algorithm, as described above in more detail in reference to FIG. 1. Vector output 510 may represent a vector output generated representing a user input 136. Vector output 510 representing a user input 136 may be generated utilizing any of the methodologies as described above in more detail. Referring now to FIG. 5B, vector output 515 may represent an updated vector output generated for the physiological state for the user, utilizing the vector output 510 representing a user input 136. Computing device 104 utilizes the updated vector output 515 to identify a recommendation 156 for a user. A recommendation 156 includes any of the recommendation 156 as described above in more detail in reference to FIGS. 1-4.

Figure 6:
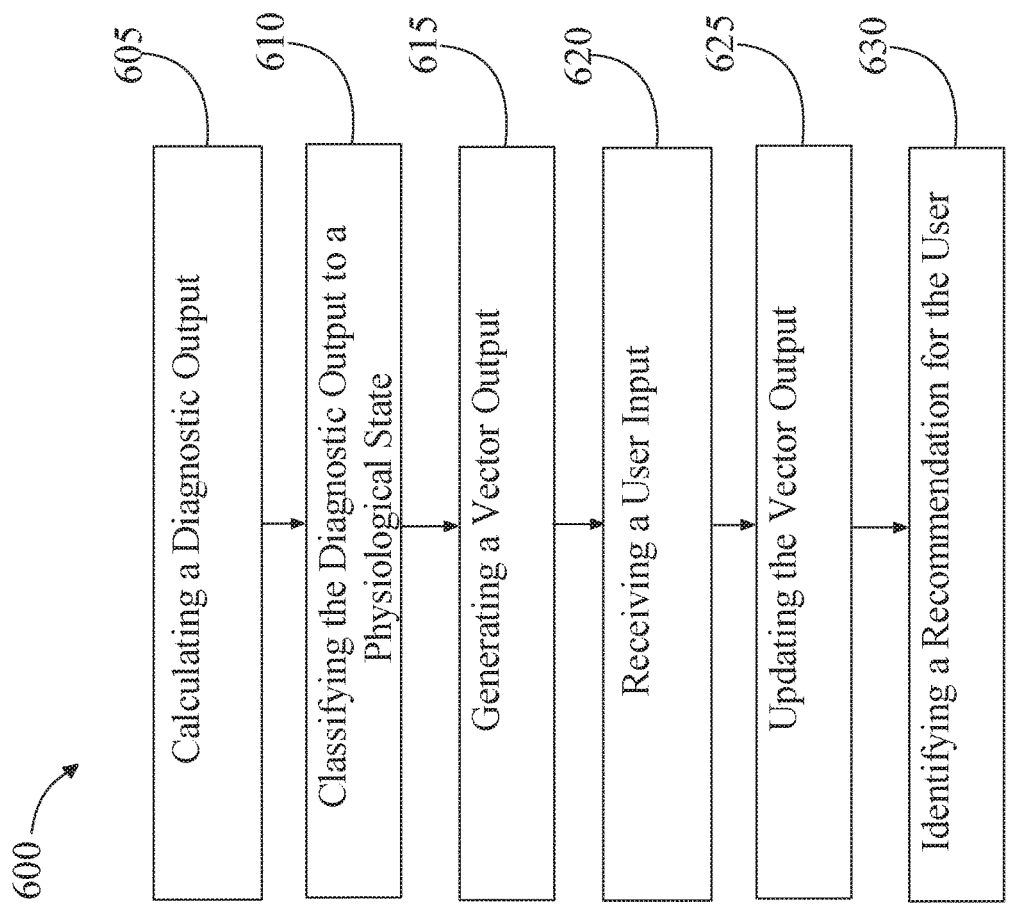
FIG. 6 is a process flow diagram illustrating an exemplary embodiment of a method of dynamic conditional guidance using artificial intelligence.

Referring now to FIG. 6, an exemplary embodiment of a method 600 of dynamic conditional guidance using artificial intelligence is illustrated. At step 605, computing device 104 calculates a diagnostic output 108 using a biological extraction related to a user. A diagnostic output 108 includes any of the diagnostic output 108 as described above in more detail in reference to FIG. 1. A biological extraction includes any of the biological extractions as described above in more detail in reference to FIG. 1. For instance and without limitation, a biological extraction may include a saliva sample analyzed for one or more markers of toxicity. In yet another non-limiting example, a biological extraction may include a urine sample analyzed for iodine levels. Diagnostic output 108 is generated using a first machine-learning process 120. A first machine-learning process 120 includes any of the machine-learning processes as described above in more detail in reference to FIG. 1. For example, a first machine-learning process 120 may include a supervised machine-learning process. In yet another non-limiting example, a first machine-learning process 120 may include a lazy-learning process. A diagnostic output 108 identifies a prognostic label and an ameliorative label. A prognostic label includes any of the prognostic labels as described above in more detail in reference to FIG. 1. For instance and without limitation, a prognostic label may identify a future probable medical condition of a user such as myocardial infarction, based on a biological extraction showing extremely high levels of lipoprotein (a). An ameliorative label may identify one or more lifestyle modifications to reduce a user's risk of myocardial infarction, such as by taking a ubiquinol supplement and taking high doses of soluble fiber.

With continued reference to FIG. 6, at step 610, computing device 104 classifies, using a physiological classifier 124 and a first classification algorithm, a diagnostic output 108 to a physiological state for the user. Physiological classifier 124, includes any of the classifiers as described above in more detail in reference to FIG. 1. A first classification algorithm includes any of the classification algorithms as described above in more detail in reference to FIG. 1. For instance and without limitation, a classification algorithm may include a Naïve-Bayes classification algorithm or a k-nearest neighbor algorithm. A physiological state for a user 128 includes any of the physiological states as described above in more detail in reference to FIG. 1. A physiological state of a user includes any characterization as to the overall current health of an individual. For instance and without limitation, a physiological state may indicate that a user is in excellent physical and poor mental health. In an embodiment, a physiological state of a user may indicate the overall health of a user based on a numerical scale. For example, a physiological state of a user may be graded on a sliding scale from 0 to 100, where 0 may indicate that the user is in extremely poor overall health, while 100 may indicate that the user is in excellent and top health. Physiological states may be determined based on one or more expert inputs, as described above in more detail in reference to FIGS. 1-3.

With continued reference to FIG. 6, at step 615, computing device 104 generates a vector output for the physiological state for a user 128, using a clustering algorithm. A vector output, includes any of the vector outputs as described above in more detail in reference to FIG. 1. A vector output may be represented in n dimensional space. A vector output may be generated using a clustering algorithm. A clustering algorithm includes any of the clustering algorithms as described above in more detail in reference to FIG. 1. For instance and without limitation, a clustering algorithm may include a k-means clustering, a mean-shift clustering, a density based spatial clustering of applications with noise (DBSCAN), an expectation-maximization (EM) clustering using Gaussian mixture models (GMM), an agglomerative hierarchical clustering, and the like.

With continued reference to FIG. 6, computing device 104 generates a plurality of vector outputs containing physiological states, using training data and a clustering algorithm. Training data, includes any of the training data as described above in more detail in reference to FIGS. 1-5. In an embodiment, a plurality of vector outputs may be generated, whereby each vector output of a plurality of vector outputs may represent a different physiological state. For example, a first vector output may represent a physiological state of an individual who is in poor overall health, while a second vector output may represent a physiological state of an individual who is in mediocre overall health. Computing device 104 converts a physiological state for a user 128 to a vector output for the user. This may be performed utilizing any of the methodologies as described above in more detail in reference to FIG. 1. Computing device 104 calculates a distance between a plurality of vector outputs containing physiological states and a vector output for a user. Distance may be calculated utilizing any of the methodologies as described above in more detail in reference to FIGS. 1-5. Computing device 104 select a vector output from a plurality of vector outputs containing physiological states utilizing the calculated distance. In an embodiment, computing device 104 may select a vector output that s located the shortest and/or smallest distance between a vector output for a user and a vector output from within a plurality of vector outputs.

With continued reference to FIG. 6, at step 620, computing device 104 receives a user input 136 generated in response to a diagnostic output 108. A user input 136, includes any of the user input 136 as described above in more detail in reference to FIGS. 1-5. Computing device 104 may receive a user input 136 from a remote device 140 operated by a user, utilizing any network methodology as described herein. Computing device 104 may receive a user input 136 entered by a graphical user interface 144 located on computing device 104. In an embodiment, a user input 136 may describe a user response to an ameliorative label. For example, an ameliorative label generated by computing device 104 may recommend a user to consume twenty grams of beta glucan per day. In such an instance, a user may generate a user response, detailing that the user has only been consuming 5 grams of beta glucan per day. Computing device 104 classifies a user input 136, using a health classifier, and a second classification algorithm to determine a health impact of the user input 136. Health classifier includes any classifier as described above in more detail in reference to FIG. 1. Health classifier utilizes a user input 136 as an input, and outputs a health impact of the user input 136. A health impact includes any of the health impacts as described above in more detail in reference to FIG. 1. For example, a health classifier may identify that a user input 136 that contains a remark that the user reads three books for pleasure each month as a positive health impact. In yet another non-limiting example, health classifier may determine that a user input 136 that contains a remark that the user has gained an excessive amount of weight as a negative health impact. Computing device 104 adjusts a vector output based on a health impact of a user 148 impact. For example, a health impact that has a negative health impact on a user may negatively affect a vector output, while a health impact that has a neutral health impact may not change a vector output.

With continued reference to FIG. 6, at step 625 computing device 104 updates a vector output using a user input 136. Updating a vector output may include changing the distance, length, and/or location of a vector output using a user input 136. For example, a user input 136 that negatively impacts a user's health may cause a vector output to retract and be smaller in size. In yet another non-limiting example, a user input 136 that positively impacts a user's health may cause a vector output to expand in size and lengthen. Vector output may be updated utilizing any of the methodologies as described above in more detail in reference to FIG. 1.

With continued reference to FIG. 6, at step 630 computing device 104 identifies a recommendation 156 for a user, utilizing an updated vector output. Computing device 104 may identify a recommendation 156 utilizing a control vector output 160. A control vector output 160 includes any of the control vector output 160 as described above in more detail in reference to FIG. 1. Computing device 104 locates a control vector output and evaluates the distance between an updated vector output and the control vector output 160. Distance may be measured utilizing any of the distance measurements as described above in more detail in reference to FIGS. 1-5. Computing device 104 locates a recommendation 156 intended to minimize the distance between an updated vector output and a control vector output 160. In an embodiment, computing device 104 may represent a plurality of recommendations in n-dimensional space. Computing device 104 may locate recommendations that are located in n-dimensional space between a control vector output 160 and an updated vector output.

With continued reference to FIG. 6, computing device 104 calculates a conditional output 168 containing an indication of a conditional state of a user. A conditional output includes any of the conditional output 168 as described above in more detail in reference to FIGS. 1-5. Computing device 104 generates a conditional output 168 using a second machine-learning process 164. A second machine-learning process 164 includes any of the machine-learning processes as described above in more detail in reference to FIG. 1. In an embodiment, a conditional output 168 may specify on a numerical score, the conditional state of a user. For example, a conditional output 168 may specify on a scale from 0 to 100 that a user has a score of 89, indicating that the user's overall health score in very good, and also indicating that the user's updated conditional vector output is getting closer to a control vector output 160.

With continued reference to FIG. 6, computing device 104 is configured to convert a user input 136 to a user vector output. A user vector output may be generated utilizing any of the methodologies as described above in more detail in reference to FIGS. 1-5. Computing device 104 calculates an ameliorative vector output for an ameliorative label. This may be performed utilizing any of the methodologies as described above in more detail in reference to FIGS. 1-5. Computing device 104 analyzes the distance between a user vector output and an ameliorative vector output. Computing device 104 analyzes the distance by measuring the distance utilizing any of the measurements as described above in more detail in reference to FIGS. 1-5. Computing device 104 generates a recommendation 156 for a user based on the distance between a user vector output and an ameliorative vector output. Recommendation 156 may be generated, such as by locating recommendation 156 represented in n dimensional space that are located between a user vector output and an ameliorative vector output. In an embodiment, a recommendation may be transmitted to remote device 140 operated by a user. In an embodiment, a recommendation may be transmitted to a third-party device operated by an informed advisor. A recommendation may be transmitted utilizing any network methodology as described herein.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
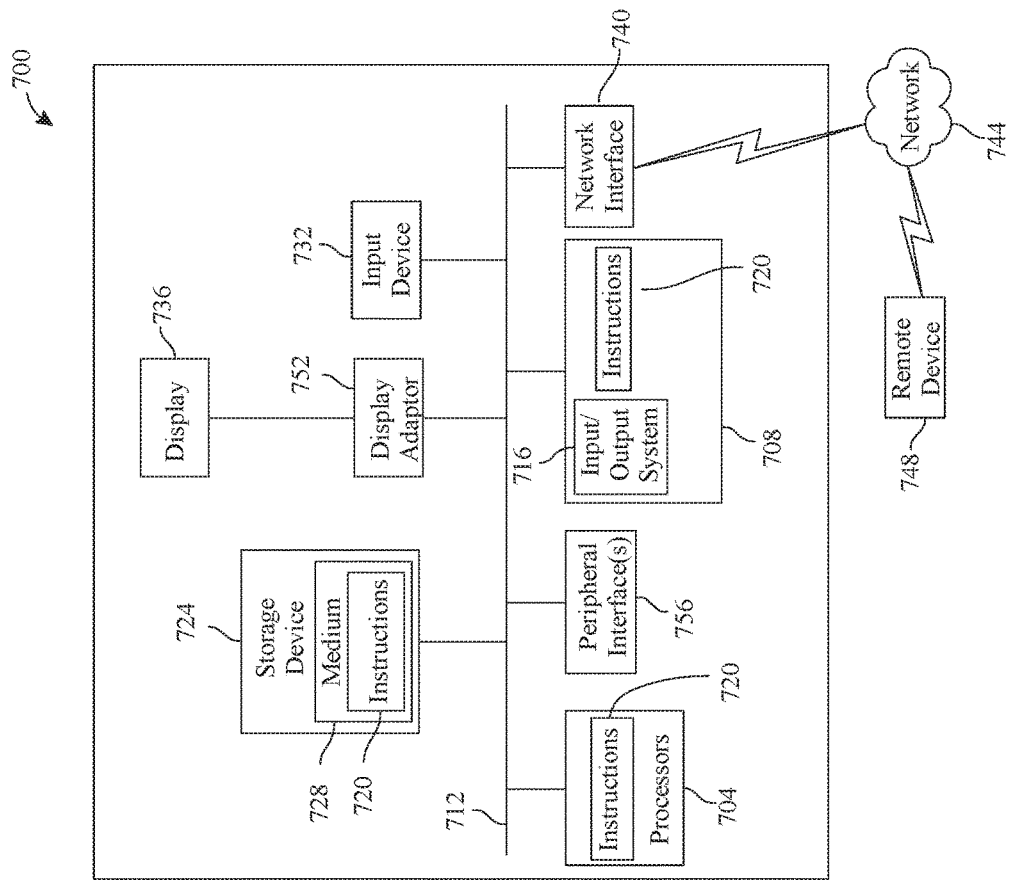
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Memory 708 may include various components (e.g., machine-readable media) including, but not limited to, a random access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for dynamic conditional guidance using artificial intelligence, the system comprising a computing device, the computing device designed and configured to:
    calculate a diagnostic output using a biological extraction related to a user and a first machine-learning process, wherein the diagnostic output identifies a prognostic label and an ameliorative label, wherein the prognostic label is a medical condition affecting the user, wherein the ameliorative label is configured to alleviate the medical condition affecting the user;
    receive training data, wherein receiving the training data further comprises receiving a first training set including a plurality of data entries, wherein each first data entry of the plurality of first data entries comprising at least an element of physiological state data and at least a correlated first prognostic label, wherein the physiological state data comprises descriptions of the user's physiological state entered by the user;
    generate a machine learning model using the first machine-learning process, wherein generating the machine learning model comprises an input layer of nodes, at least one intermediate layers, and an output layer of nodes, wherein a connection between nodes is created, wherein the connections between nodes in adjacent layers are adjusted to produce desired values at the output nodes;
    outputting, using the machine learning model, the diagnostic output;
    classify, using a physiological classifier and a first classification algorithm, the diagnostic output to a physiological state for the user, wherein the first classification algorithm derives from the training data a physiological classifier, wherein the physiological classifier utilizes the diagnostic output as an input and outputs a physiological state, and wherein the physiological classifier is iteratively updated using classification data as a function of the training data;
    generate a vector output for the physiological state for the user using a clustering algorithm;
    receive a user input generated in response to the diagnostic output;
    update the vector output using the user input; and
    identify a recommendation for the user, utilizing the updated vector output.

2. The system of claim 1, wherein the first classification algorithm further comprises a Naïve-Bayes classification algorithm.

3. The system of claim 1, wherein the first classification algorithm further comprises a K-nearest neighbor algorithm.

4. The system of claim 1, wherein the computing device is further configured to:
    generate a plurality of vector outputs containing physiological states utilizing training data and the clustering algorithm;
    convert the physiological state for the user to a vector output for the user;
    calculate a distance between the plurality of vector outputs containing physiological states and the vector output for the user; and
    select a vector output from the plurality of vector outputs utilizing the distance.

5. The system of claim 1, wherein the computing device is further configured to:
    classify the user input, using a health classifier and a second classification algorithm, to determine the health impact of the user input; and
    adjust the vector output based on the health impact of the user input.

6. The system of claim 1, wherein the user input is generated in response to the ameliorative label.

7. The system of claim 1, wherein the user input further comprises a second biological extraction.

8. The system of claim 1, wherein the computing device is further configured to:
    identify a control vector output;
    evaluate the distance between the updated vector output and the control vector output; and
    locate a recommendation to minimize the distance.

9. The system of claim 8, further comprising calculating a conditional output utilizing the distance between the updated vector output and the control vector output, wherein the conditional output contains an indication of a conditional state of the user, and the conditional output is generated using a second machine-learning process.

10. The system of claim 1, wherein the computing device is further configured to:
    convert the user input to a user vector output;
    calculate an ameliorative vector output for the ameliorative label;
    analyze the distance between the user vector output and the ameliorative vector output; and
    generate a recommendation for the user based on the distance between the user vector output and the ameliorative vector output.

11. A method of dynamic conditional guidance using artificial intelligence, the method comprising:
calculating by a computing device, a diagnostic output using a biological extraction related to a user and a first machine-learning process, wherein the diagnostic output identifies a prognostic label and an ameliorative label, wherein the prognostic label is a medical condition affecting the user, wherein the ameliorative label is configured to alleviate the medical condition affecting the user;
receiving by the computing device, training data, wherein receiving the training data further comprises receiving a first training set including a plurality of data entries, wherein each first data entry of the plurality of first data entries comprising at least an element of physiological state data and at least a correlated first prognostic label, wherein the physiological state data comprises descriptions of the user's physiological state entered by the user;
generating by the computing device, a machine learning model using the first machine-learning process, wherein generating the machine learning model comprises an input layer of nodes, at least one intermediate layers, and an output layer of nodes, wherein a connection between nodes is created, wherein the connections between nodes in adjacent layers are adjusted to produce desired values at the output nodes;
outputting by the computing device, using the machine learning model, the diagnostic output;
classifying by the computing device, using a physiological classifier and a first classification algorithm, the diagnostic output to a physiological state for the user wherein the first classification algorithm derives from the training data a physiological classifier, wherein the physiological classifier utilizes the diagnostic output as an input and outputs a physiological state, and wherein the physiological classifier is iteratively updated using classification data as a function of the training data;
generating by the computing device, a vector output for the physiological state for the user using a clustering algorithm;
receiving by the computing device, a user input generated in response to the diagnostic output;
updating by the computing device, the vector output using the user input; and
identifying by the computing device, a recommendation for the user, utilizing the updated vector output.

12. The method of claim 11, wherein the first classification algorithm further comprises a Naïve-Bayes classification algorithm.

13. The method of claim 11, wherein the first classification algorithm further comprises a K-nearest neighbor algorithm.

14. The method of claim 11, wherein generating the vector output further comprises:
generating a plurality of vector outputs containing physiological states utilizing training data and the clustering algorithm;
converting the physiological state for the user to a vector output for the user;
calculating a distance between the plurality of vector outputs containing physiological states and the vector output for the user; and
selecting a vector output from the plurality of vector outputs utilizing the distance.

15. The method of claim 11, receiving the user input further comprises:
classifying the user input, using a health classifier and a second classification algorithm, to determine the health impact of the user input; and
adjusting the vector output based on the health impact of the user input.

16. The method of claim 11, wherein the user input is generated in response to the ameliorative label.

17. The method of claim 11, wherein receiving the user input further comprises receiving a second biological extraction.

18. The method of claim 11, wherein identifying the recommendation for the user further comprises:
identifying a control vector output;
evaluating the distance between the updated vector output and the control vector output; and
locating a recommendation to minimize the distance.

19. The method of claim 18, further comprising calculating a conditional output utilizing the distance between the updated vector output and the control vector output, wherein the conditional output contains an indication of a conditional state of the user, and the conditional output is generated using a second machine-learning process.

20. The method of claim 11, wherein identifying the recommendation further comprises:
converting the user input to a user vector output;
calculating an ameliorative vector output for the ameliorative label;
analyzing the distance between the user vector output and the ameliorative vector output; and
generating a recommendation for the user based on the distance between the user vector output and the ameliorative vector output.

* * * * *